US00PP25823P3

(12) United States Plant Patent
Klemm et al.

(10) Patent No.: US PP25,823 P3
(45) Date of Patent: Aug. 18, 2015

(54) ***PETUNIA* PLANT NAMED 'KLEPH12220'**

(50) Latin Name: ***Petunia* hybrid**
Varietal Denomination: KLEPH12220

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 189 days.

(21) Appl. No.: 13/987,042

(22) Filed: Jun. 27, 2013

(65) Prior Publication Data
US 2015/0020269 P1 Jan. 15, 2015

(51) Int. Cl.
*A01H 5/02* (2006.01)

(52) U.S. Cl.
USPC ..... Plt./356.2

(58) Field of Classification Search
USPC ..... Plt./356.1, 356.13, 356.17, 356.2
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new *Petunia* plant particularly distinguished by violet flowers with dark eyes, foliage having strong vein expression, a compact form, and a semi-trailing habit, is disclosed.

1 Drawing Sheet

Genus and species: *Petunia* hybrid.
Variety denomination: 'KLEPH12220'.

BACKGROUND OF THE NEW PLANT

The present invention comprises a new and distinct variety of *Petunia*, botanically known as *Petunia* hybrid, and hereinafter referred to by the variety name 'KLEPH12220'. 'KLEPH12220' originated from a cross-pollination conducted in July 2008 in Stuttgart, Germany between the proprietary female *Petunia* variety 'R 44' (unpatented), having purple flowers and the proprietary male *Petunia* variety 'PH 2007 0027' (unpatented), having white flowers.

The seeds from the cross were sown and plants were grown in a greenhouse for evaluation, where an individual plant designated 'KLEPH12220' was selected from the group of plants in April 2009, having violet flowers with dark eyes, a compact form, and a semi-trailing habit. In April 2009, 'KLEPH12220' was first vegetatively propagated by terminal tip cuttings and tissue culture. 'KLEPH12220' was found to reproduce true to type in successive generations of asexual propagation via tissue culture and terminal tip cuttings in Stuttgart, Germany.

CROSS REFERENCE TO RELATED APPLICATIONS

Plant Breeder's Rights for 'KLEPH12220' were applied for in Canada on Feb. 8, 2013, Application No. 13-7926. 'KLEPH12220' has not been made publicly available or sold more than one year prior to the filing date of this application.

SUMMARY

The following are the most outstanding and distinguishing characteristics of this new variety when grown under normal horticultural practices in Stuttgart, Germany.

1. Violet flowers with dark eyes;
2. Foliage having strong vein expression;
3. A compact form; and
4. A semi-trailing habit.

DESCRIPTION OF THE PHOTOGRAPH

This new *Petunia* plant is illustrated by the accompanying photograph which shows a close-up of the plant's foliage and flowers.

The photograph is of a five-month-old plant grown in a glass greenhouse in Stuttgart, Germany in May 2012.

The colors shown are as true as can be reasonably obtained by conventional photographic procedures.

DESCRIPTION OF THE NEW VARIETY

The following detailed descriptions set forth the distinctive characteristics of 'KLEPH12220'. The data which define these characteristics were collected from asexual reproductions carried out in Latina, Italy. Data was collected on plants grown ten weeks from cultivation from potting in a glass greenhouse in Latina, Italy in April 2013. Color references are to The R.H.S. Colour Chart of The Royal Horticultural Society of London (R.H.S.), 5$^{th}$ edition (2007).

Classification:
- *Family*.—Solanaceae.
- *Botanical*.—*Petunia* hybrid.
- *Common*.—*Petunia*.
- *Designation*.—'KLEPH12220'.

Parentage:
- *Female parent*.—The proprietary female *Petunia* variety 'R 44' (unpatented).
- *Male parent*.—The proprietary male *Petunia* variety 'PH 2007 0027' (unpatented).

Plant:
- *Form*.—Compact.
- *Habit*.—Semi-trailing.

*Height* (*from top of soil*).—About 20.0 cm.
*Width* (*horizontal plant diameter*).—About 40.0 cm.
*Propagation*.—Terminal tip cuttings.
*Time to produce a finished flowering plant*.—8 weeks from potting, in Spring.
*Time to initiate and develop roots*.—2 to 3 weeks.
*Root description*.—Moderate density, moderate branching, white roots.

Stems:
*Average number* (*basal*).—10.
*Length of basal branches* (*from the base of the stem to the tip*).—About 20.0 cm.
*Internode length*.—1.5 cm to 2.0 cm.
*Diameter of branches* (*from midpoint*).—0.3 cm.
*Stem color*.—RHS 143A.
*Anthocyanin*.—Absent.
*Texture*.—Pubescent.

Leaves:
*Arrangement*.—Alternate at the base of the stems, opposite on the flower stems.
*Length*.—3.5 cm to 3.8 cm.
*Width*.—2.8 cm.
*Shape*.—Broad elliptic.
*Apex*.—Acute-mucronate.
*Base*.—Rounded.
*Margin*.—Entire.
*Immature leaf color*.—Upper surface: RHS 137C. Lower surface: RHS 138B.
*Mature leaf color*.—Upper surface: RHS N137C. Lower surface: RHS 138B.
*Texture* (*both upper and lower surfaces*).—Slightly pubescent.
*Venation pattern*.—Pinnate.
*Venation color*.—Upper surface: RHS N137C. Lower surface: RHS 138B.
*Petioles*.—Length: 1.5 cm to 2.0 cm. Diameter: 0.3 cm. Color: RHS N137C. Texture: Slightly pubescent.

Flower buds:
*Shape*.—Irregular oblong.
*Length*.—3.5 cm to 4.0 cm.
*Diameter*.—0.6 cm.
*Color at tight bud*.—RHS 144A.
*Texture*.—Slightly pubescent.

Inflorescence:
*Blooming habit* (*flowering season*).—Permanent flowering during summer time.
*Inflorescence type*.—Cymose.
*Number of flowers per node*.—1.
*Lastingness of individual blooms on the plant*.—About 7 days.
*Fragrance*.—Absent.
*Flowers*.—Arrangement: Composed of 5 petals fused at the base. Shape: Funnel form. Diameter (flower face): About 6.0 cm. Depth (total length of flower): About 5.5 cm. Throat/Funnel: Length: About 3.0 cm. Diameter (at opening): 1.5 cm to 2.0 cm. Texture (both inner and outer surfaces): Smooth, glabrous. Color, inner surface: RHS N92A with RHS N81A veins. Color, outer surface: RHS 76C with RHS N79A veins. Color, immature petals: Upper surface and margins: RHS N155C with RHS N81A veins. Lower surface: RHS 157B and RHS N79A veins. Color, mature petals: Upper surface: RHS 78C with RHS N81B margins and RHS N81A veins. Lower surface: RHS 76B with RHS 76A margins and RHS N79A veins. Petals: Apex: Obtuse to mucronate. Base: Fused. Margin: Entire. Strength of waviness: Weak. Degree of lobation: Weak. Calyx arrangement: Actinomorphic, composed of 5 sepals. Sepals: Color: Upper surface: RHS 137C. Lower surface: RHS 138B. Length: 2.5 cm. Width: 0.4 cm. Shape: Narrowly oblong. Apex: Acute. Base: Cuneate. Margin: Entire. Texture (both upper and lower surfaces): Slightly pubescent.
*Pedicels*.—Color: RHS N137C. Length: 3.5 cm to 4.0 cm. Diameter: 0.2 cm. Texture: Slightly pubescent.

Reproductive organs:
*Stamens*.—Quantity: 5. Shape: Needle with elliptic head. Filament: Length: 1.0 cm to 1.5 cm. Diameter: About 0.05 cm. Color: RHS 145D. Anther: Shape: Elliptic. Color: RHS 112A. Length: 0.2 cm. Diameter: 0.1 cm. Pollen: Color: RHS 189B. Amount: Abundant.
*Pistils*.—Quantity per flower: 1. Length: 1.5 cm. Stigma color: RHS N189B. Style color: RHS 145D.

Fruit and seed set: No fruit and seed set observed.
Disease and pest/insect resistance: No disease and pest/insect resistance observed.

COMPARISON WITH PARENTAL LINES AND KNOWN VARIETY

'KLEPH12220' is a distinct variety of *Petunia* having violet flowers with dark eyes, a compact form, and a semi-trailing habit and is distinguished from its parents as described in Table 1.

TABLE 1

Comparison with Parental Lines

| Characteristic | 'KLEPH12220' | Female Parent 'R 44' | Male Parent 'PH 2007 0027' |
|---|---|---|---|
| Corolla color | Violet with dark eyes | Purple | White |

'KLEPH12220' is a distinct variety of *Petunia* violet flowers with dark eyes, a compact form, and a semi-trailing habit and is most similar to the commercial *Petunia* variety 'KLEPH07119' (U.S. Plant Pat. No. 20,143). Differences between the varieties are described in Table 2.

TABLE 2

Comparison with Similar Variety

| Characteristic | 'KLEPH12220' | 'KLEPH07119' |
|---|---|---|
| Vein expression | Stronger vein and darker color | Lighter colored veins |

We claim:

1. A new and distinct variety of *Petunia* plant designated 'KLEPH12220' as illustrated and described herein.

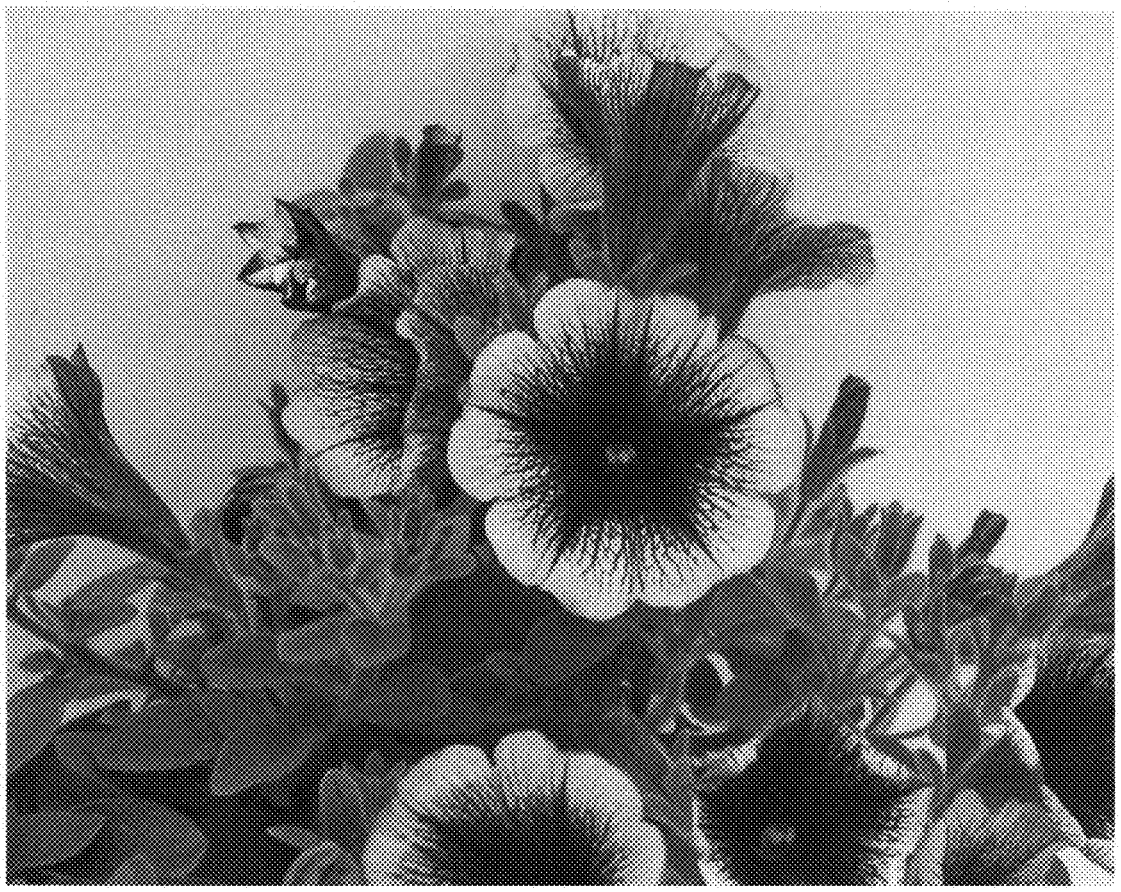

* * * * *